United States Patent
Thies et al.

(10) Patent No.: US 11,400,184 B2
(45) Date of Patent: Aug. 2, 2022

(54) METHOD OF MAKING AN OSTEOCONDUCTIVE POLYMER ARTICLE AND AN OSTEOCONDUCTIVE POLYMER ARTICLE THUS MADE

(71) Applicants: DSM IP Assets B.V., Heerlen (NL); ACADEMISCH ZIEKENHUIS MAASTRICHT, Maastricht (NL)

(72) Inventors: Jens Christoph Thies, Echt (NL); Ruud Jozef Regina Wilhelmus Peters, Echt (NL); Pieter J. Emans, Maastricht (NL); Jacob Koenen, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 158 days.

(21) Appl. No.: 16/753,351

(22) PCT Filed: Oct. 5, 2018

(86) PCT No.: PCT/EP2018/077213
§ 371 (c)(1),
(2) Date: Apr. 3, 2020

(87) PCT Pub. No.: WO2019/068903
PCT Pub. Date: Apr. 11, 2019

(65) Prior Publication Data
US 2020/0316259 A1 Oct. 8, 2020

(30) Foreign Application Priority Data
Oct. 6, 2017 (EP) .................................... 17195323

(51) Int. Cl.
*A61L 27/46* (2006.01)
*A61L 27/44* (2006.01)
(Continued)

(52) U.S. Cl.
CPC ............. *A61L 27/46* (2013.01); *A61L 27/446* (2013.01); *A61L 27/54* (2013.01); *A61L 27/56* (2013.01);
(Continued)

(58) Field of Classification Search
None
See application file for complete search history.

(56) References Cited

U.S. PATENT DOCUMENTS

| 4,739,013 A | 4/1988 | Pinchuk |
| 4,810,749 A | 3/1989 | Pinchuk |

(Continued)

FOREIGN PATENT DOCUMENTS

| CN | 101274108 A | 10/2008 |
| CN | 101274108 A | 10/2008 |

(Continued)

OTHER PUBLICATIONS

English language translation of WO 02/070031 A1. (Year: 2002).*
(Continued)

*Primary Examiner* — Dominic Lazaro
(74) *Attorney, Agent, or Firm* — Kevin M. Bull

(57) ABSTRACT

The disclosure relates to methods of making an osteoconductive polymer article for use as an orthopedic implant comprises steps of forming an article from a biocompatible, non-biodegradable polymer, the article comprising a non-flat surface with roughness Ra of at least 5 µm; providing a dispersion of bioactive ceramic particles of particle size at most 10 µm in a first solvent comprising a solvent for the polymer; coating at least the non-flat surface with the dispersion in at least one step; and rinsing the coated article with a second solvent being a non-solvent for the polymer to substantially remove the first solvent. Further disclosed is an osteoconductive polymer article for use as an orthopedic
(Continued)

implant, which article is made from a biocompatible, non-biodegradable polymer and comprises a non-flat surface with roughness Ra of at least 5 μm, wherein bioactive ceramic particles of particle size at most 10 μm are partly embedded in the polymer at the surface of the article. The methods exhibit benefits in ease of modifying a surface layer with bioactive particles, applying mild conditions and not requiring use of further additives or post-treatments, or without significantly affecting bulk polymer properties, and result in an orthopedic implant article having particles adhering to the surface while still being accessible for interaction with surrounding tissue or fluid.

19 Claims, 4 Drawing Sheets

(51) Int. Cl.
*A61L 27/56* (2006.01)
*A61L 27/54* (2006.01)
*C08L 75/04* (2006.01)

(52) U.S. Cl.
CPC ....... *A61L 2420/02* (2013.01); *A61L 2420/04* (2013.01); *A61L 2430/02* (2013.01); *C08L 75/04* (2013.01)

(56) References Cited

U.S. PATENT DOCUMENTS

| | | | |
|---|---|---|---|
| 5,133,742 | A | 7/1992 | Pinchuk |
| 5,229,431 | A | 7/1993 | Pinchuk |
| 8,562,647 | B2 | 10/2013 | Kaiser et al. |
| 2006/0216321 | A1 | 9/2006 | Lyu |
| 2009/0088858 | A1* | 4/2009 | Zinger ............... B24C 1/06 623/18.11 |
| 2011/0022085 | A1 | 1/2011 | Murphy et al. |
| 2016/0144066 | A1 | 5/2016 | Long et al. |
| 2016/0271296 | A1 | 9/2016 | Jongpaiboonkit et al. |
| 2016/0287242 | A1 | 10/2016 | Troxel et al. |

FOREIGN PATENT DOCUMENTS

| | | | |
|---|---|---|---|
| DE | 10055465 A1 | 11/2000 | |
| JP | H06339521 | 12/1994 | |
| JP | H06339521 A | 12/1994 | |
| JP | H06339522 | 12/1994 | |
| JP | H06339522 A | 12/1994 | |
| WO | WO0048552 A1 | 8/2000 | |
| WO | WO02070031 | 9/2002 | |
| WO | WO-02070031 A1 * | 9/2002 | ........... A61L 27/443 |
| WO | WO2014/060591 A1 | 4/2014 | |

OTHER PUBLICATIONS

Chetty et al. 2007, Hydroxyapatite-coated polyurethane for auricular cartilage replacement: An in vitro study, Journal Biomedical Materials Research Part A, 2007, pp. 475-482, (DOI 10.1002/jbm.a).

Davison, et al., In vivo performance of microstructured calcium phosphate formulated in novel water-free carriers, Acta Biomaterialia 8, 2008, pp. 2759-2769, (DOI: 10.1016/j.actbio.2012.04.007).

Dorozhkin, S.V., Calcium orthophosphate deposits: Preparation, properties and biomedical applications, Materials Science and Engineering C, 2015, 272-326, C55.

Geary et al. Mater. Sci: Mater. Med (2008) 19:3355-3363 (DOI 10.1007/s10856-008-3472-8).

Li et al., Biomedical coatings on polyethylene terephthalate artificial ligaments, Journal of Biomedical Materials Research A, Feb. 2015, pp. 839-845, vol. 103 A, Issue 2 (DOI: 10.1002/jbm.a.35218).

Li et al., Enhancement of the osseointegration of a polyethylene terephthalate artificial ligament graft in a bone tunnel using 58S bioglass, International Orthopaedics (SICOT), 2012, pp. 191-197, (DOI: 10.1007/s00264-011-1275-x).

Li et al., Hydroxyapatite coating enhances polyethylene terephthalate artificial ligament graft osseointegration in the bone tunnel, International Orthopaedics, 2010, pp. 1561-1567, (DOI: 10.1007/s00264-010-1158-6.

Pfeiffer, et al., The histologic and biomechanical response of two commercially available small glenoid anchors for use in labral repairs, Journal of Shoulder and Elboe Surgery, .2014, pp. 1156-1161, DOI: 10.1016/j.ise.2013.12.036).

Chen, Q.Z., et al., "Bioactive and Mechanically Strong Bioglass®-Poly(D,L-Lactic Acid) Composite Coatings on Surgical Sutures", Dept. of Materials and Centre for Tissue Engineering and Regenerative Medicine, Imperial College London, UK (2005).

* cited by examiner

A

B

METHOD OF MAKING AN OSTEOCONDUCTIVE POLYMER ARTICLE AND AN OSTEOCONDUCTIVE POLYMER ARTICLE THUS MADE

CROSS-REFERENCE TO RELATED APPLICATIONS

This application is a U.S. national phase entry under 35 USC 371 of international application PCT/EP2018/077213, filed 5 Oct. 2018, which designated the U.S. and claims priority to European Application 17195323.5, filed 6 Oct. 2017, the entire contents of each of which is hereby incorporated by reference in its entirety.

FIELD

The disclosed inventions pertain to methods of making a polymer article for use as a medical implant showing osteoconductive properties, especially to making a polyurethane article having bioactive inorganic particles like calcium phosphates at its surface to enhance bone growth on the article after implantation. The inventions also relate to such polymeric articles and to their use in medical implants.

BACKGROUND

An orthopedic implant is a medical device manufactured to for example replace a missing joint or bone, to support a damaged bone, or to act as support and anchor for artificial cartilage. Medical implants like orthopedic implants, tendons and ligaments, or dental implants generally require proper integration with the patient's bone tissue. From biological perspective, the ideal material for such reconstructive surgery is autogenic bone or tissue, because of biocompatibility, osteoconductivity, osteoinductivity and lack of immunogenic response. Limitations in harvesting adequate amounts of tissue or bone material and disadvantages of multiple operations, however, make the 'ideal' material far from ideal for many surgical procedures. An alternative is using allogeneic and xenogeneic bone-derived grafts, but such materials may induce disease transfer, high immunogenic response, or show unreliable degradation behavior. Therefore, synthetic implant materials or biomaterials, like metals, ceramics, polymers and composites, find increasing use in clinical applications. Bioactive materials, meaning osteoconductive materials onto which bony tissue can grow and bond, include calcium phosphates like hydroxyapatite, mixed inorganic oxides like Bioglass®, some polymers, and composites of polymer and such inorganic materials. Advantages of composite materials include the option to tailor properties by varying composition and addition of further compounds, and freedom in design and shaping.

Polymer-ceramic composites as bioactive material may be made by mechanical mixing of polymer and ceramic particles, generally resulting in a polymer continuous matrix with ceramic particles dispersed therein. Mixing may be done by processing in the melt state of the polymer, but also in solution or dispersion to allow lower processing temperature.

In WO2000/048552 a method of making a polymer-ceramic composite is described, wherein first a polymer-ceramic mixture is made of a biocompatible polymer and micron-sized ceramic particles, wherein polymer and particles are chemically coupled, and which mixture is then subjected to shock compaction. This process would result in a composite wherein the components are substantially integrated and attached to each other, showing improved stiffness, strength, and impact resistance.

DE10055465 discloses a composite composition for bone replacement comprising a biocompatible thermoplastic polymer as matrix and inorganic non-metallic bioactive particles, like PEEK filled with calcium phosphate or biocompatible glass particles. The document further describes a method of making a bone-replacement implant by laser-induced sintering of such composition, that is by a rapid prototyping- or 3D printing-like process.

US2006/0216321 describes a method of making an osteoconductive load-bearing implant, wherein micron-sized natural bone material is mixed with a biocompatible polymer in a solvent, the mixture is formed into the shape of the implant, and solvent is removed from the implant.

Such polymer-ceramic composites may show improved properties versus the polymer as such because the ceramic particles may for example act as reinforcing filler. If only osteoconduction is aimed at, change of polymer properties may not be needed or even not be desired. Another disadvantage of such composites may be that the ceramic particles are fully covered by or embedded in the polymer, and not available at the surface of an implant for interacting with tissue. In such case a surface treatment of the implant may be needed to induce bioactivity, for example selectively etching the polymer surface to expose part of the ceramic particles.

Incorporating ceramic particles into a polymer may also negatively affect properties, for example by inducing polymer degradation. For example, Geary et al. describe in Mater. Sci: Mater. Med (2008) 19:3355-3363 (DOI 10.1007/s10856-008-3472-8) that polycarbonate polyurethanes, like commercially available Bionate® grades, are suitable materials for use as in vivo biomedical devices, for example in replacing diseased or damaged joints. This Geary publication discloses incorporating hydroxyapatite (HA) particles in such polycarbonate polyurethanes via a compounding step. This bulk modification results in different mechanical properties of the polymer material, but promotes degradation resulting in significant reduction in molar mass of the polymer. In addition, the particles being dispersed throughout the polymer does not mean that particles are available at the surface for interaction with tissue or fluid after implantation, as particles are likely covered by a layer of polymer.

An alternative approach to making osteoconductive implants is surface modification of a pre-formed polymer article. For example, Chetty et al. describe an auricular implant in J. Biomed. Mater. Res. Part A 2007 475-482 (DOI 10.1002/jbm.a), which is made by coating an aliphatic polycarbonate polyurethane article with a layer of HA via a 'solvent-compression method'. In this method, the article is coated by immersing in cyclohexanone to tackify the surface, making an assembly by placing the article between two layers of HA powder, placing the assembly in a die and compressing by applying a load, removing the assembly from the die and drying at elevated temperature, and extracting residual cyclohexanone with water. This process resulted in a HA coating layer with thickness of about 94 µm that adhered to the surface and showed bioactivity in in vitro testing. It is mentioned that thinner layers are difficult to achieve, whereas articles of complex shape would be difficult to coat with such compression method.

US2016/0271296 addresses the problem that an article made from some biocompatible polymers like polyetheretherketone (PEEK) are difficult to coat with inorganic minerals like HA. The method proposed to make a mineral coated article comprises steps of i) coating the article with a primer coating composition comprising a polymer, especially polycaprolactone, ii) contacting the coated article with a modified simulated body fluid (SBF), and iii) incubating the coated article and SBF to form the mineral coated article by a mineralization process. Such biomineralization process requires well-controlled conditions and is generally lengthy, taking up to 40 days.

In WO2014/060591 another route to making a coating of a bone substitute material on a PEEK article is described, wherein particles of highly porous silica gel, into which HA is embedded, is used as bone substitute material. This porous material is applied to the surface, which may first have been hydrophilized with an oxygen plasma, and then the polymer surface is briefly melted resulting in penetration of molten polymer into pores of the silica particles and in partial sinking of the particles in the PEEK surface. The particles would well adhere to the article and protrude from the polymer in the range of 0.01-50 µm.

SUMMARY

Despite numerous publications on making a polymer article showing osteoconductive properties for use as a medical implant, including above cited documents, there is still a need in industry for a simple method to provide a polymer article with a surface that shows bioactivity and preferably allows osseointegration after implantation. It is an object of present disclosure to provide such method and such polymer article for use as a component of or as a medical device.

The embodiments as described herein below and as characterized by the claims provide such method to make a polymer article with a surface that shows bioactivity and allows osseointegration after implantation.

In accordance with an embodiment of the invention, a method of making an osteoconductive polymer article for use as an orthopedic implant comprises steps of
Forming an article from a biocompatible, non-biodegradable polymer, the article comprising a non-flat surface with roughness Ra of at least 5 µm;
Providing a dispersion of bioactive ceramic particles of particle size of at most 10 µm in a first solvent comprising a solvent for the polymer;
Coating at least the non-flat surface with the dispersion in at least one step; and
Rinsing the coated article with a second solvent being a non-solvent for the polymer to substantially remove the first solvent;
to result in particles being partly embedded in the polymer at the surface of the article.

In accordance with another embodiment, an osteoconductive polymer article for use as (a component of) an orthopedic implant is provided, which article is made from a biocompatible, non-biodegradable polymer and comprises a non-flat surface with roughness Ra of at least 5 µm, wherein bioactive ceramic particles of particle size <10 µm are partly embedded in the polymer at the surface of the article.

The methods disclosed herein may exhibit benefits in ease of modifying a surface layer with bioactive particles, applying mild conditions and not requiring use of further additives or post-treatments, or without significantly affecting bulk polymer properties, and may result in an article having particles adhering to the surface while still being accessible for interaction with surrounding tissue or fluid.

BRIEF DESCRIPTION OF FIGURES

The invention will be further elucidated by the following illustrative figures, without being restricted thereto.

DETAILED DESCRIPTION OF EMBODIMENTS

Figure 1:
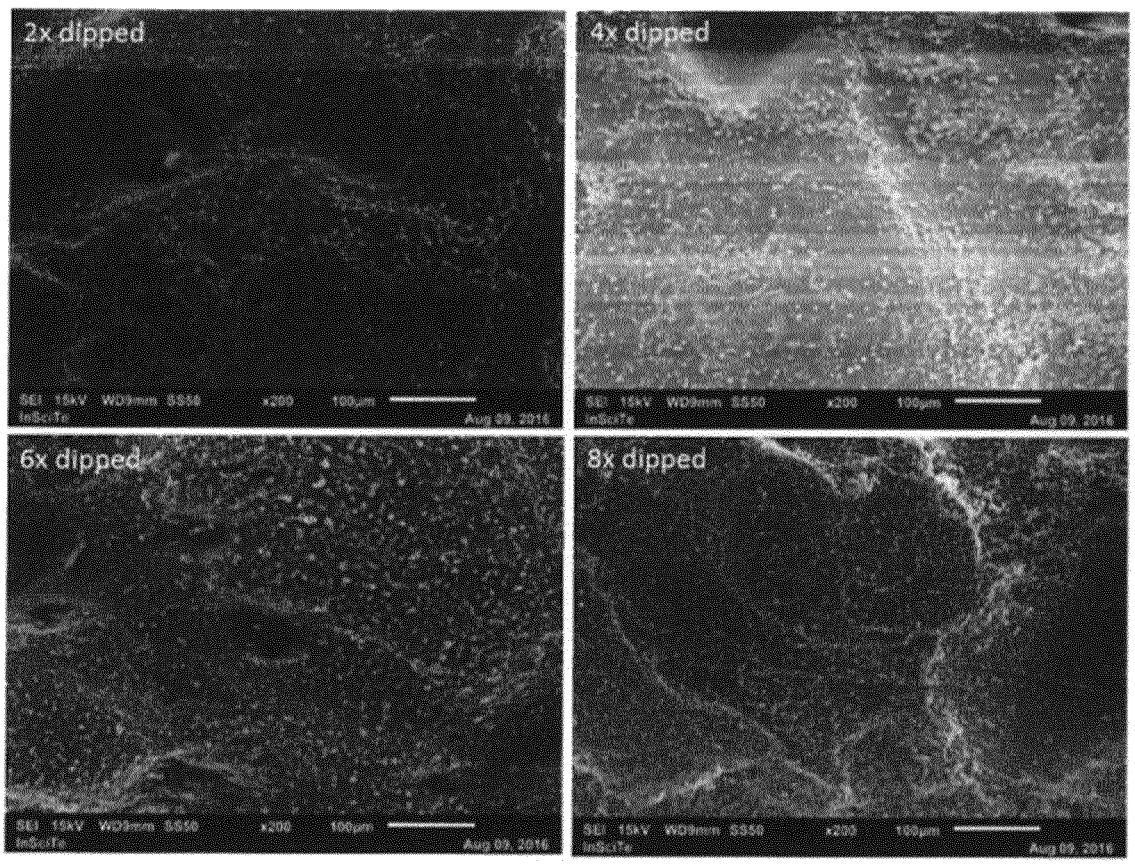
FIG. 1 shows SEM micrographs of the surface of MP4 samples after different number of dipping steps with BCP particles dispersion in THF.

Within the context of present disclosure, a biocompatible material or compound means that the substance is biologically compatible by not producing a toxic, injurious, or immunologic response in living tissue. Biodegradable means a material is susceptible to chemical degradation or decomposition into simpler components by biological means, such as by an enzymatic or hydrolytic action under normal physiological conditions; and is also referred to as bio-resorbable. Biostable herein means a material is not biodegradable (also called non-biodegradable or non-bioresorbable).

Bioactivity is the ability of a material to elicit a specific biological response at the interface of the material and cells, body fluid or tissue, due to its reactive surface. In case of osteoconductivity, bioactivity results in growth of bony tissue onto the surface or into the porous structure of an implant or graft. Osseointegration refers to the formation of a direct interface between an implant and bone tissue, without intervening soft tissue, and resulting in mechanical anchorage of the implant; i.e., the functional result of an osteoconductive implant. Osteogenesis is formation of bone or development of bones, while osteoinduction refers to the act or process of stimulating osteogenesis.

In accordance with an embodiment of the invention, a method of making an osteoconductive polymer article for use in or as an orthopedic implant comprises steps of
Forming an article from a biocompatible, non-biodegradable polymer, the article comprising a non-flat surface with roughness Ra of at least 5 µm;
Providing a dispersion of bioactive ceramic particles of particle size of at most 10 µm in a first solvent comprising a solvent for the polymer;
Coating at least the non-flat surface with the dispersion in at least one step; and
Rinsing the coated article with a second solvent being a non-solvent for the polymer to substantially remove the first solvent;
to result in particles being partly embedded in the polymer at the surface of the article.

Basically, a polymer article is provided having a surface with protruding and/or exposed ceramic particles adhered to it, which article can be used as part of an implant or as an implant onto which bone tissue may grow.

Orthopedic implants are used in orthopedic surgery concerning conditions that involve the musculosketetal system, which provides for form, stability and movement of the body. It is made up of the body's bones (the skeleton), muscles, cartilage, tendons, ligaments, joints, and other connective tissue (the tissue that supports and binds tissues and organs together). The musculoskeletal system's primary functions include supporting the body, allowing motion, and protecting vital organs. The joints and musculoskeletal tissues of the human body may be subject to traumatic injury and disease and degenerative processes that over a period of time can lead to the deterioration or failure of the joint causing severe pain or immobility. Generally, the ability of a joint to provide pain free articulation and carry load is dependent upon the presence of healthy bone, cartilage and associated musculoskeletal tissues that provide a stable joint. In connection with present disclosure orthopedic surgery also relates to maintaining the motion in the various joints of the human body. Examples of orthopedic implants include those used in partial or total joint arthroplasty, knee and hip prostheses, and osteochondral implants Further examples include bone anchors, plugs and screws, which are used to fixate implants like artificial ligaments and tendons, meniscus or labrum replacement devices, or cartilage replacement devices to bone.

The method of making an osteoconductive polymer article for use as an orthopedic implant comprises a step of forming an article from a polymer, which forming step can include any known polymer processing and shaping method. Suitable forming methods depend amongst others on the type of polymer used and on the desired shape of the article, and may include compression molding, injection molding, extrusion molding, forming semi-finished articles in combination with post-machining, stereolithography, and 3D printing. The forming methods may result in a solid nonporous article, or in a porous article. A porous article may for example be formed with a molding process applying a foaming agent, or by 3D printing. For processing of thermoplastic polymers, injection molding and 3D printing techniques are suited, also offering possibilities to make articles with complex shape and comprising more than one type of polymer. Articles comprising more than one polymer or component may be made by combining multiple formed parts by e.g. welding or using adhesives, but also by multi-component molding techniques like multi-shot or co-injection molding, sandwich molding, over-molding, or by 3D printing.

The article formed in present method comprises at least one non-flat surface, meaning that such surface is not smooth but has certain roughness, resulting from for example irregularities, unevenness, projections, pits, or holes. Surface roughness can be measured using known techniques such as described in the experiments and is characterized by roughness Ra of at least 5 μm. The article itself is typically also not flat but may comprise a substantially cylindrical part or other curved surface, with dimensions generally on the order of mm's.

In an embodiment of the present method, the polymer article formed is non-porous, or has at least a non-porous textured surface with roughness Ra of at least 5 μm. In further embodiments, said at least one textured surface has roughness Ra of at least 6, 8, 10, 12, 14, 16, 18, or 20 μm. The textured surface may also be defined by the VDI 3400 scale, which is an industry standard for defining the surface texture of for example metal molds for producing plastic parts having such texture. In further embodiments, the article is formed from a polymer applying a mold having a surface texture of at least VDI 3400.34, or at least VDI 3400.36, 38, 40, 42, 44, or 45.

In an embodiment, the polymer article formed and having said surface roughness is porous or has at least one porous surface. The average size of the pores at the surface, or optionally within the bulk of the article, is at least 5, 10, 20, 50, 100, or 200 μm. This results in a porous surface with certain roughness and increases available surface area of the article, but also allows bodily fluids entering pores and bone growth into the article. Too large pores may reduce mechanical stability of the article. In further embodiments the average size of the pores at the surface, or optionally within the bulk of the article, is at most 500, 400, 300 or 200 μm.

In an embodiment of the present method, an article is formed from a biocompatible polymer. The polymer may be thermoplastic or thermosetting, and its chemical composition may vary widely. Biocompatible polymers that are used in medical implants include natural, semi-synthetic and synthetic polymers. Natural biocompatible polymers include materials like silk, elastin, collagen, casein, gelatin, albumin, keratin, chitin or chitosan, and natural or modified polysaccharides like cellulose and starch. Semi-synthetic biocompatible polymers include materials like derivates of proteins and polysaccharides, such as carboxy methylcellulose. Synthetic biocompatible polymers include materials like epoxides, poly(meth)acrylates, fluoropolymers, silicone polymers, polyurethanes, polyesters, polyethers, polyolefins, vinyl polymers, polysulfones, polyacetals, polyimides, polyamides, polycarbonates, polyaryletherketones, and copolymers, as well as compounds and blends thereof. Such synthetic polymers may be based on natural compounds like amino acids and/or on synthetic monomers. A biocompatible polymer may be biodegradable, for example aliphatic polyesters like polylactic acid, polyglycolic and their copolymers, or non-biodegradable.

In embodiments of present inventions non-biodegradable polymers, also referred to as not bio-erodible or non-resorbable polymers, are applied for forming the article. Suitable polymers, or suitable compositions or compounds based on such polymers, have mechanical properties, especially strength and modulus, that are in ranges compatible with, or even matching those of bodily tissues like bone and cartilage. The polymer can be a homopolymer, a copolymer, or a block copolymer. The biocompatible, non-biodegradable polymer can be selected from polyolefins, polystyrenes, polyacrylates, polysiloxanes, polyethers, polyaryletherketones, polyesters, polyamides, and polyurethanes.

In an embodiment, the polymer used in present method is a block copolymer. Block copolymers or segmented copolymers are polymers comprising blocks or segments of oligomers or polymers that are chemically distinct, and typically show different thermal and mechanical properties. Often the blocks in a block copolymer comprising two (or more) types of blocks are referred to as being 'hard' and 'soft' polymer blocks, and show microphase separation. The hard block in a block copolymer typically comprises a rigid or high modulus semi-crystalline or amorphous polymer, with a melting temperature (Tm) or a glass transition temperature (Tg) higher than the use temperature, of e.g. about 35° C. The soft block in the block copolymer often comprises a flexible, amorphous polymer with a Tg lower than 35° C., preferably lower than 0° C. Thermal parameters like Tm and Tg are generally determined on dry samples; using well-known techniques like DSC or DMA. In such phase-separated block copolymers, the hard segments function as physical crosslinks for the flexible soft segments, resulting in materials having properties that can range from fairly stiff to flexible and elastic, depending on the ratio of hard to soft segments. When such block copolymer is heated above the softening point of the hard blocks, it will become a viscous fluid and may be processed into an article of desired shape and will solidify upon cooling. Such thermoplastic block copolymers showing elastomeric character are generally referred to as thermoplastic elastomers, or TPEs.

In an embodiment, the polymer used in present method is a TPE material. The TPE may comprise hard and soft blocks, wherein the hard block comprises a polymer chosen from the group consisting of polyesters, polyamides, polystyrenes, polyacrylates, polyurethanes and polyolefins; and the soft block comprises a polymer chosen from the group consisting of polyethers, polyesters, polyacrylates, polyolefins and polysiloxanes. Such polymers are understood herein to include homopolymers and copolymers, and polyesters are considered to include polycarbonates. Examples of TPE block copolymers are copolyester esters, copolyether esters, and copolycarbonate esters, wherein the hard blocks typically are based on polybutylene terephthalate (PBT); copolyester amides and copolyether amides; copolymers containing polystyrene hard blocks and copolyethylene-butadiene soft blocks (SEBS) or isobutylene soft blocks (SIBS); and polyurethanes comprising hard blocks based on diisocyanates and chain extenders, and polyester, polyether or polysiloxane soft blocks.

In embodiments of the present inventions, a polyurethane, more specifically a polyurethane block copolymer, is applied as biocompatible polymer. The term polyurethanes denotes a family of polymers basically including three principle components; that are a polyol or macroglycol, a diisocyanate and a chain extender. Polyurethanes have a backbone that includes urethane groups and often also urea groups in the repeating units of the polymer, resulting from reaction of diisocyanate with a diol and/or diamine as chain extender. Suitable diisocyanates include aromatic, aliphatic and cycloaliphatic compounds. Chain extenders are typically aliphatic compounds of low molar mass, having two or more hydroxyl or amine groups. Bifunctional chain extenders result in linear, thermoplastic polymers, whereas multifunctional chain extenders lead to crosslinked, thermoset products. When also a polyol is used a block copolymer or TPE results, with the polyol as soft block and hard blocks formed by the urethane (and optionally urea) units. Generally known polyurethane block copolymers and methods to prepare these copolymers are described in a.o. U.S. Pat. Nos. 4,739,013, 4,810,749, 5,133,742 and 5,229,431.

In embodiments of the present method, the polyurethane TPE may comprise as soft block an aliphatic polyester diol, an aliphatic polyether diol, or a polysiloxane diol. As for chain extenders, also an amine-functional soft block can be used, resulting in urea instead of urethane linkages. Biocompatibility and biostability of various polyurethane block copolymers in the human body is proven, and a polyurethane block copolymer can be chosen to have such composition that the mechanical properties of an orthopedic implant made therefrom resembles the mechanical properties of bone, but also of cartilage. Properties may be tailored by varying chemical compositions and/or molar masses of the blocks. The hard blocks of the block copolymer, including polyurethane TPE, used in the method of the invention may have a molar mass of about 160 to 10,000 Da, and preferably of about 200 to 2000 Da. The molar mass of the soft segments is typically about 200 to 100,000 Da, and preferably about 400 to 9000 Da. The ratio of soft to hard blocks can be chosen to result in certain stiffness or hardness of the polymer. Typically, durometer hardness as measured with the Shore test using A or D scales, may be from 40 ShA, or at least 50 or 60 ShA and up to 80 or 75 ShD, generally representing a flexural modulus range of 10-2000 MPa.

In further embodiments, the polyurethane TPE, also referred to as TPU, comprises an aliphatic polyester as soft block, more specifically an aliphatic polycarbonate. Suitable aliphatic polyesters are generally made from at least one aliphatic dicarboxylic acid and at least one aliphatic diol, which components are preferably chosen such that an essentially amorphous oligomer or polymer is formed having a Tg below 10, 0, or −10° C. Aliphatic polycarbonate diols are based on similar aliphatic diols as used for polyester diols, and can be synthesized via different routes. A suitable example is poly(hexamethylene carbonate)diol. Such polycarbonate urethanes are suitably used for biomedical applications, in view of their flexibility, strength, biostability, biocompatibility and wear resistance. In an embodiment, the biocompatible polymer for forming the article may be a blend of two or more polymers, and may comprise one or more additives. Examples of additives are anti-oxidants, processing aids, lubricants, surfactants, antistatic agents, colorants, radiopaque agents, and fillers. Fillers can include inorganic particles or fibrous material, for example to increase stiffness of the article. A mineral filler like bismuth oxide, barium sulphate or calcium phosphates may be applied as a radiopaque additive, to also result in the article to be visible at X-ray images as an implant. The additives may be present in the typically effective amounts as known in the art, such as 0.01-25 mass % or 0.1-10 mass % based on the amount of the polymer.

In another embodiment, the article is made from a composition substantially consisting of polymer and containing substantially no additives.

In an embodiment, the method optionally comprises a step of rinsing the formed article. Such rinsing step aims to remove any compounds or contamination potentially present, that would not comply with requirements for medical implants. Rinsing may be performed with a single solvent, but also with multiple solvents in sequential steps, wherein each subsequent rinsing applies a solvent miscible with the preceding solvent. Solvents of different polarities may thus be used, like a sequence ethanol-isopropanol-hexane-isopropanol-ethanol. This multiple rinsing allows removal of potentially present compounds of different solubilities. The skilled person can select suitable solvents, depending on the situation. In an embodiment, the final rinsing is done with 96% ethanol.

The method of making an osteoconductive polymer article for use as an orthopedic implant comprises providing a dispersion of bioactive ceramic particles in a first solvent. Suitable bioactive ceramic particles for use in present methods include all inorganic materials that show the capability of direct bonding to living bone, for example by formation of biologically active bone-like apatite through chemical reaction of the particle surface with surrounding body fluid. Examples of suitable materials include various calcium phosphates and so-called bioactive glass. Barrère et al. describe in *Int. J. Nanomedicine* 2006:1(3), 317-332 various types of calcium phosphates, like dicalcium phosphate anhydrate ($CaHPO_4$; DCPA), dicalcium phosphate dihydrate ($CaHPO_4.2H_2O$; DCPD), octacalcium phosphate ($Ca_8(HPO_4)_2.5H2O$; OCP), tricalcium phosphate ($Ca_3(PO_4)_2$; TCP), and hydroxyapatite ($Ca_{10}(PO_4)_6(OH)_2$; HA). Also blends of different types may be applied, or even show advantages; like mixtures of HA and TCP or of HA and bioactive glass. The ceramic particles may in addition to their main constituents comprise small or trace amounts of other (inorganic) elements or ions, like Na, Mg, Fe, Zn, Ti, Ag, Cu or $—SO_4$, or $—CO_3$, which may improve specific properties of the particles.

Bioactive glass, including commercial Bioglass® products, refers to mixed inorganic oxides that have a surface-reactive glass film compatible with tissues; and may be used as a surface coating in some types of medical and dental implants. The Bioglass® 45S5 grade, for example, is indicated to be a glass composed of 45 mass % $SiO_2$, 24.5 mass % CaO, 24.5 mass % $Na_2O$, and 6.0 mass % $P_2O_5$. The high ratio of calcium to phosphorus in this material would promote formation of apatite crystals; calcium and silica ions can act as crystallization nuclei. Glasses are non-crystalline amorphous solids that are commonly composed of silica-based materials with minor amounts of other inorganic elements.

In an embodiment, the bioactive ceramic particles have a particle size in the range 0.1-10 µm. Particle size and size distribution can be measured with SEM or optical microscopy, or with (laser) light diffraction techniques. Within present disclosure the d50 value as measured with light diffraction according to ISO 13320:2009, e.g with a Malvern Mastersizer 2000, is defined as the particle size of the bioceramic particles. The particle size does not appear to be specifically critical, but larger particles may be more effective in interacting with body fluid and cells. A stable dispersion of large particles in a relatively low viscous solvent on the other hand may be more difficult to make than of particles of for example nano-size range. In other embodiments of the present method, ceramic particles having size of at least 200 nm, or at least 300, 400, or 500 nm are used. Further embodiments of the method use ceramic particles having size of at most 10, 8, 6, 5, 4, 3, 2 µm, or at most 1 µm.

In embodiments of the present method, a dispersion of bioactive ceramic particles in a first solvent is provided that comprises about 1-20 mass % of ceramic particles. It was found that a relatively high concentration of particles in the dispersion may result in high surface coverage, but may have disadvantages of high viscosity, dispersion instability or non-homogeneous coating and surface coverage. Therefore, use of dispersions comprising at most 18, 15 or 10 mass % of ceramic particles is preferred. As very low particle concentrations result in low surface coverage, the dispersion used preferably comprises at least 1.5, 2, or 2.5 mass % of ceramic particles.

The method of making an osteoconductive polymer article for use as an orthopedic implant further comprises providing a dispersion of bioactive ceramic particles in a first solvent comprising a solvent for the polymer. The person skilled in the art will be able to select a suitable solvent for a given polymer based on his general knowledge, optionally supported by some literature; for example on solubility parameters of solvents and polymers, like in the "Polymer Handbook" by Brandrup and Immergut, Eds. For a so-called good solvent for a polymer, interactions between polymer chain and solvent molecules are energetically favorable, and difference between solubility parameter of polymer and solvent is small. A solvent for a polymer can substantially dissolve the polymer, optionally by applying some heating. The solubility or maximum concentration of polymer in this first solvent does not need to be high; a few mass % being dissolvable already represents a solvent for the polymer. The first solvent may be a single solvent or a mixture of solvents, including good solvents for the polymer, less good solvents for the polymer and non-solvents for the polymer, for reasons as further discussed hereafter.

In an embodiment of the method, the first solvent substantially or completely consists of a solvent for the polymer. This allows a relatively simple process, and short contacting times of particle dispersion with the surface of the polymer article to effectively modify the surface.

In another embodiment, the first solvent comprises a solvent for the polymer and a non-solvent of the polymer, wherein the solvents are miscible. It was observed that a good solvent for the polymer may, in addition to swelling a surface layer, also solubilize the layer; which may result in ceramic particles being completely covered or embedded by polymer. It has been surprisingly found that varying the composition of such first solvent mixture, provides the skilled person with a tool to influence the degree of surface swelling and thus of embedding of the ceramic particles in the surface layer of the polymer article; to preferably result in particles that are partially embedded in polymer for good adhesion to the article's surface, while not being fully covered by a polymer film and thus directly being exposed to its environment and accessible for interaction with body fluid after implantation. As further illustrated by the experiments, the skilled person can find proper solvent combinations for the first solvent based on his knowledge and with some experimental work. Preferably, the non-solvent has a lower boiling point, that is higher rate of evaporation, than the solvent for the polymer. Without wishing to be bound to any theory, the inventors reason that upon evaporating of non-solvent a relatively small amount of solvent for the polymer remains at the surface, which results in a swollen surface layer and the particles partly sinking into and being partly embedded in the polymer surface. In this respect, it is noted that a first solvent mixture that is not a solvent for the polymer as such, will only result in particles being embedded if a solvent composition that is able to swell the polymer surface is formed during the process at the surface of the article, e.g. by evaporation of non-solvent. The first solvent may comprise a solvent and a non-solvent for the polymer in widely varying ranges, like 98-2 vol % of solvent for the polymer, or at most 90, 80, 70, 70, 60, 50, 40, 30, 20, 10, 5 or at most 2 vol % of solvent for the polymer, based on total amount of first solvent.

In embodiments of the method, for example, wherein the polymer is a polyurethane or a polyurethane block copolymer, the first solvent comprises as solvents for the polymer compounds like tetrahydrofuran (THF), methyl-tetrahydrofuran (m-THF), dimethylformamide (DMF), dimethylacetamide (DMAc), dimethylsulfoxide (DMSO), dioxane, dioxolane, or mixtures thereof. Suitable non-solvents for the first solvent include for example lower aliphatic alcohols like ethanol, aliphatic esters, aliphatic ether, and lower alkanes and alkenes. As indicated above, the non-solvent can preferentially evaporate from a mixture forming the first solvent during the method. This is further illustrated by experiments wherein DMF/EtOH mixtures gave better results than a THF/EtOH mixtures.

In embodiments of the method, the first solvent substantially consists of solvent and optionally non-solvent for the polymer.

In an embodiment of the present method, a dispersion of bioactive ceramic particles in a first solvent is made by known means. For example, a dispersion is made using mechanical stirring means, such as by applying high speed and/or high shear stirring; preferably without addition of additives like dispersion aids or surfactants. This has the advantage that the implant will also not comprise such additives, although the dispersion may show settlement caused by density differences of ceramic particles and first solvent. For this last reason, the dispersion is typically being stirred until shortly before using the dispersion to coat the article.

In an embodiment, the method applies a dispersion substantially consisting of bioactive ceramic particles and first solvent.

In another embodiment of the present method, a dispersion of bioactive ceramic particles in a first solvent is made by mechanical means, for example by applying high speed and/or high shear stirring, with addition of effective amounts of biocompatible additives like dispersion aids or surfactants to stabilize the dispersion thus made.

In further embodiments, sonication is applied before and/or during making a ceramic particle dispersion to help disaggregation of possibly present aggregates of particles and their dispersion.

The method of making an osteoconductive polymer article for use as an orthopedic implant further comprises coating at least the non-flat surface with the dispersion in at least one step. Different ways of coating the surface can be applied in present method. Based on the foregoing discussion and the illustrating experiments provided hereinafter, the skilled person will be able to select a suitable method and conditions that will result in particles becoming partly embedded in the polymer; also depending on the shape of the article, the polymer to be coated and the first solvent used. Suitable coating methods include dip coating and spray coating. Such coating methods allow to apply a thin layer of the dispersion on the surface of a complex shaped article within short time, optionally using multiple coating steps with intermediate drying, and with controllable contact time before removing excess dispersion or removing at least part of the first solvent, e.g. by drying/evaporating and/or by rinsing with a second solvent. Coating can be suitable performed at ambient conditions, but for example the temperature may also be increased to shorten drying times.

In an embodiment of the method, coating is done by dip coating the article having at least one non-flat surface with the dispersion in at least one step. In order to prevent particles becoming fully embedded in the polymer, coating time is preferably kept short. Suitable time for a dip coating step, that is the time the article is submerged in the dispersion, include periods of about 1-10 s. It was found to be beneficial to apply multiple short dip coating steps to obtain a certain coverage of the surface with ceramic particles, rather than aiming to obtain a certain coverage in one or two steps. In preferred embodiments therefore, the method comprises at least 3, 4, 5, 6, 7, 8, 9 or 10 dip coating steps, optionally using intermediate drying periods to remove at least part of the first solvent. A drying period can vary from 1 to 10 min, depending on conditions and volatility of first solvent (or solvents contained therein). Suitable temperature for coating and drying is from 10 to 150° C., also depending of softening temperature of the polymer article, and is typically about 40-60° C., optionally in combination with reduced pressure and/or inert gas, like nitrogen flow.

In further embodiments, treating with bioceramic particles dispersion may be done in multiple steps applying different dispersions; that is dispersions comprising different bioceramic particles. The particles may for example differ in their chemical composition, and/or in particle size. In case bioceramic particles of different size are used, the dispersion having largest particles is preferably used first, and smallest particles are used in a last treating step. Such multi-step approach may result in more effective surface coverage, while also resulting in smaller particles being exposed on the surface.

In case of spray coating, applying multiple thin layers with preferably intermediate drying is preferred over applying one thick coating layer, for similar reasons as mentioned for dip coating.

The method of making an osteoconductive polymer article for use as an orthopedic implant further comprises rinsing the coated article with a second solvent being a non-solvent for the polymer to substantially remove the first solvent. This rinsing step aims to completely remove residual first solvent and possible other compounds, to make an article that will comply with requirements for medical implants. Treating the modified polymer surface with non-solvent for the polymer may also further stabilize the morphology obtained. Rinsing may be performed with a single second solvent, but also with multiple second solvents in sequential steps, wherein the first second solvent applied is miscible with the first solvent, and each subsequent rinsing applies a second solvent miscible with the preceding second solvent. The second solvent may consist of a single solvent but may also comprise a mixture of compounds. Second solvents of different polarities may thus be used, like a sequence ethanol-isopropanol-hexane-isopropanol-ethanol. Such multiple rinsing allows removal of potentially present compounds of different solubilities. The skilled person can select suitable second solvents, including the non-solvents for the polymer as described above, depending on the situation. In an embodiment, the final rinsing is done with 96% ethanol.

The method of making an osteoconductive polymer article for use as an orthopedic implant results in bioactive ceramic particles present at the surface of the article, which particles are partly embedded in the polymer. The partially embedded particles adhere to the polymer surface yet are exposed at the surface, that is they are accessible for direct interaction with body fluid or fluid. Stated otherwise, the ceramic particles are not covered by a thin polymer layer that would prevent such direct interaction.

In another embodiment, the present disclosure provides an osteoconductive polymer article for use as (a component of) an orthopedic implant as obtainable by, or obtained by, the method as herein described. This osteoconductive polymer article shows all features as described hereinabove for the method of making the article, including any combination of features; unless such combination would be clearly physically impossible.

In accordance with a further embodiment, an osteoconductive polymer article for use as a component of an orthopedic implant or as an orthopedic implant is provided, which article has been made from a biocompatible, non-biodegradable polymer and which article comprises at least a non-flat surface with roughness Ra of at least 5 µm, in which surface bioactive ceramic particles of average particle size of at most 10 µm are present that are partly embedded in the polymer. The article has bioactive particles adhering to the surface that are accessible for interaction with surrounding tissue or fluid when being used as an implant. This osteoconductive polymer article shows the features as described hereinabove for the method of making the article, including any combination of features; unless such combination would be clearly physically impossible.

In another embodiment, the present disclosure relates to the use of an osteoconductive polymer article as obtainable by or obtained by the method as herein described as an orthopedic implant.

In another embodiment, the present disclosure relates to the use in or as an orthopedic implant of an osteoconductive polymer article made from a biocompatible, non-biodegradable polymer and which article comprises at least a non-flat surface with roughness Ra of at least 5 µm, in which surface bioactive ceramic particles of average particle size of at most 10 µm are partly embedded in the polymer.

In further embodiments, the present disclosure relates to orthopedic implants comprising an osteoconductive polymer article as obtainable by or obtained by the method as herein described as an orthopedic implant.

In further embodiments, the present disclosure relates to orthopedic implants comprising an osteoconductive polymer article made from a biocompatible, non-biodegradable polymer and which article comprises at least a non-flat surface with roughness Ra of at least 5 µm, in which surface bioactive ceramic particles of average particle size of at most 10 µm are partly embedded in the polymer.

Examples of orthopedic implants comprising an osteoconductive polymer article as described herein include those used in partial or total joint arthroplasty, knee and hip prostheses, and osteochondral implants. Further examples include bone anchors, plugs and screws, which are used to fixate implants like artificial ligaments and tendons, meniscus or labrum replacement devices, or cartilage replacement devices to bone.

Any one of the embodiments, aspects and preferred features or ranges as disclosed in this application may be combined in any combination, unless stated otherwise herein or if technically clearly not feasible to a skilled person. Various aspects of the invention are further summarized in the below set of embodiments.

101. A method of making an osteoconductive polymer article for use as an orthopedic implant comprises steps of
  Forming an article from a biocompatible, non-biodegradable polymer, the article comprising a non-flat surface with roughness Ra of at least 5 µm;
  Providing a dispersion of bioactive ceramic particles of particle size of at most 10 µm in a first solvent comprising a solvent for the polymer;
  Coating at least the non-flat surface with the dispersion in at least one step; and
  Rinsing the coated article with a second solvent being a non-solvent for the polymer to substantially remove the first solvent;
  to result in particles being partly embedded in the polymer at the surface of the article.
102. The method of embodiment 101, wherein the orthopedic implant is selected from the group consisting of partial or total joint arthroplasty, knee and hip prostheses, osteochondral implants, bone anchors, plugs and screws, meniscus or labrum replacement devices, and cartilage replacement devices.
103. The method of embodiment 101 or 102, wherein forming an article is done by compression molding, injection molding, extrusion molding, forming semi-finished articles in combination with post-machining, stereolithographic forming, or 3D printing.
104. The method of any one of embodiments 101-103, wherein forming results in a non-porous article or in a porous article, and surface roughness results from irregularities, unevenness, projections, pits, or holes.
105. The method of any one of embodiments 101-104, wherein the article formed is non-porous or has at least a non-porous textured surface with roughness Ra of at least 5 µm.
106. The method of embodiment 105, wherein the at least one textured surface has roughness Ra of at least 6, 8, 10, 12, 14, 16, 18, or 20 µm.
107. The method of embodiment 105, wherein the article having at least one textured surface is formed by applying a mold comprising a surface texture of at least VDI 3400.34, or at least VDI 3400.36, 38, 40, 42, 44, or 45.
108. The method of any one of embodiments 101-104, wherein the article formed is porous or has at least one porous surface with average size of the pores at the surface, or optionally within the bulk of the article, of at least 5, 10, 20, 50, 100, or 200 µm and of at most 500, 400, 300 or 200 µm.
109. The method of any one of embodiments 101-108, wherein the biocompatible polymer. is thermoplastic or thermosetting
110. The method of any one of embodiments 101-109, wherein the biocompatible polymer, is a natural, semi-synthetic or synthetic polymer.
111. The method of any one of embodiments 101-110, wherein the biocompatible polymer is biodegradable or non-biodegradable.
112. The method of any one of embodiments 101-111, wherein the biocompatible polymer is selected from the group consisting of polyolefins, polystyrenes, polyacrylates, polysiloxanes, polyethers, polyetheretherketones, polyesters, polyamides, and polyurethanes.
113. The method of any one of embodiments 101-112, wherein the biocompatible polymer is a block copolymer.
114. The method of embodiment 113, wherein the block copolymer comprises a flexible, amorphous polymer with a Tg lower than 35° C., preferably lower than 0° C. as soft block.
115. The method of embodiment 113 or 114, wherein the block copolymer is a thermoplastic elastomer (TPE).
116. The method of any one of embodiments 113-115, wherein the block copolymer comprises hard and soft blocks, the hard block comprising a polymer chosen from the group consisting of polyesters, polyamides, polystyrenes, polyacrylates, polyurethanes and polyolefin, and the soft block comprising a polymer chosen from the group consisting of polyethers, polyesters, polyacrylates, polyolefins and polysiloxanes.
117. The method of any one of embodiments 113-116, wherein the block copolymer is a copolyester ester, a copolyether ester, a copolycarbonate ester, a copolyester amide, a copolyether amide, a copolymer containing polystyrene hard blocks and copolyethylene-butadiene soft blocks (SEBS), or a polyurethane comprising hard blocks based on diisocyanates and chain extenders, and polyester, polyether or polysiloxane soft blocks.
118. The method of any one of embodiments 113-118, wherein the block copolymer is a polyurethane block copolymer
119. The method of embodiment 118, wherein the polyurethane comprises as soft block an aliphatic polyester diol, an aliphatic polyether diol, or a polysiloxane diol.
120. The method of any one of embodiments 113-119, wherein the block copolymer comprises hard blocks with a molar mass of about 160 to 10,000 Da, preferably of about 200 to 2,000 Da.
121. The method of any one of embodiments 113-120, wherein the block copolymer comprises soft blocks with a molar mass of about 200 to 100,000 Da, preferably of about 400 to 9000 Da.
122. The method of any one of embodiments 113-1129 wherein the block copolymer has a durometer hardness as measured with the Shore test of at least 40 ShA, preferably at least 50 or 60 ShA, and at most 80 ShD, preferably at most 75 ShD.

123. The method of any one of embodiments 113-122, wherein the block copolymer is a polyurethane TPE comprising an aliphatic polyester as soft block, preferably an aliphatic polycarbonate 124. The method of any one of embodiments 114-123, wherein the soft block is an essentially amorphous oligomer or polymer having a Tg below 10, 0, or −10° C.

125. The method of any one of embodiments 114-123, wherein the soft block is an aliphatic polycarbonate diol, preferably a poly(hexamethylene carbonate)diol.

126. The method of any one of embodiments 114-125, wherein the biocompatible polymer is a blend of two or more polymers, and optionally comprises one or more additives.

127. The method of any one of embodiments 114-125, wherein the biocompatible polymer substantially consists of polymer and contains substantially no additives.

128. The method of any one of embodiments 101-127, wherein the method further comprises a step of rinsing the formed article with a single solvent or with multiple solvents in sequential steps, wherein each subsequent rinsing applies a solvent miscible with the preceding solvent.

129. The method of any one of embodiments 101-128, wherein the bioactive ceramic particles are calcium phosphate particles, like dicalcium phosphate anhydrate ($CaHPO_4$; DCPA), dicalcium phosphate dihydrate ($CaHPO_4.2H_2O$; DCPD), octacalcium phosphate ($Ca_8(HPO_4)_2.5H2O$; OCP), tricalcium phosphate ($Ca_3(PO_4)_2$; TCP), hydroxyapatite ($Ca_{10}(PO_4)_6(OH)_2$; HA), or mixtures thereof like mixtures of HA and TCP.

130. The method of any one of embodiments 101-128, wherein the bioactive ceramic particles are so-called bioactive glass particles, that are mixed inorganic oxide particles having a surface-reactive glass film compatible with tissues, optionally mixtures of bioactive glass with other bioceramic particles like HA.

131. The method of embodiment 130, wherein the bioactive glass particles are composed of 45 mass % $SiO_2$, 24.5 mass % CaO, 24.5 mass % $Na_2O$, and 6.0 mass % $P_2O_5$.

132. The method of any one of embodiments 101-131, wherein the bioactive ceramic particles have a particle size in the range 0.1-10 μm, preferably the ceramic particles have size of at least 200 nm, or at least 300, 400, or 500 nm, and of at most 10, 8, 6, 5, 4, 3, 2 μm, or at most 1 μm.

133. The method of any one of embodiments 101-128, wherein the dispersion of bioactive ceramic particles in a first solvent comprises about 1-20 mass % of ceramic particles, preferably the dispersion comprises at most 18, 15 or 10 mass % of ceramic particles, and at least 1.5, 2, or 2.5 mass % of ceramic particles.

134. The method of any one of embodiments 101-133, wherein the first solvent substantially or completely consists of a solvent for the polymer.

135. The method of any one of embodiments 101-133, wherein the first solvent comprises a solvent for the polymer and a non-solvent for the polymer, the solvent and non-solvent being miscible.

136. The method of embodiment 135, wherein the non-solvent has a lower boiling point than the solvent for the polymer.

137. The method of any one of embodiments 135-136, wherein the first solvent comprises 98-2 vol % of solvent for the polymer, preferably at most 90, 80, 70, 70, 60, 50, 40, 30, 20, 10, 5 or at most 2 vol % of solvent for the polymer, based on total amount of first solvent.

138. The method of any one of embodiments 101-137, wherein the polymer is a polyurethane or a polyurethane block copolymer, and the first solvent comprises as solvent for the polymer tetrahydrofuran (THF), methyl-tetrahydrofuran (m-THF), dimethylformamide (DMF), dimethylacetamide (DMAc), dimethylsulfoxide (DMSO), dioxane, dioxolane, or mixtures thereof 139. The method of any one of embodiments 135-138, wherein the polymer is a polyurethane or a polyurethane block copolymer, and the first solvent comprises as non-solvent for the polymer a lower aliphatic alcohol like ethanol, an aliphatic ester, an aliphatic ether, a lower alkane or a lower and alkene.

140. The method of any one of embodiments 135-139, wherein the first solvent substantially consists of solvent and optionally non-solvent for the polymer.

141. The method of any one of embodiments 101-140, wherein the dispersion of bioactive ceramic particles in a first solvent is made using mechanical stirring means, such as high speed and/or high shear stirring, optionally with addition of effective amounts of biocompatible additives like dispersion aids or surfactants.

142. The method of any one of embodiments 141, wherein the dispersion is stirred until shortly before using the dispersion to coat the article.

143. The method of any one of embodiments 101-142, wherein the dispersion substantially consists of bioactive ceramic particles and first solvent.

144. The method of any one of embodiments 101-143, wherein coating is done by dip coating or spray coating, optionally using multiple coating steps with intermediate drying.

145. The method of any one of embodiments 101-144, wherein coating comprises at least 3, 4, 5, 6, 7, 8, 9 or 10 dip coating steps, optionally using intermediate drying periods.

146. The method of any one of embodiments 101-145, wherein coating with bioceramic particles dispersion is done in multiple steps applying different dispersions comprising different bioceramic particles, preferably particles differing in chemical composition and/or in particle size.

147. The method of embodiment 146, wherein coating is done applying different dispersions comprising bioceramic particles differing in in particle size, and wherein the dispersion having largest particles is used first, and smallest particles are used in a last treating step.

148. The method of any one of embodiments 101-147, wherein rinsing is performed with a single second solvent 149. The method of any one of embodiments 101-147, wherein rinsing is performed with multiple second solvents in sequential steps, and wherein the first second solvent applied is miscible with the first solvent, and each subsequent second solvent is miscible with the preceding second solvent.

150. The method of embodiments 149, wherein the second solvent comprises a mixture of compounds of different polarities.

151. The method of any one of embodiments 101-150, wherein a final rinsing is done with 96% ethanol.

201. An osteoconductive polymer article for use as a component of an orthopedic implant or as an orthopedic implant, the article obtainable by or obtained by the method according to embodiments 101-151.

202. An osteoconductive polymer article for use as a component of an orthopedic implant or as an orthopedic implant, which article has been made from a biocompatible, non-biodegradable polymer and which article comprises at least a non-flat surface with roughness Ra of at least 5 μm, in which surface bioactive ceramic particles of average particle size of at most 10 μm are present that are partly embedded in the polymer, and optionally has features as described in anyone of embodiments 102-151.

301. Use of the osteoconductive polymer article according to embodiment 201 or 202 as a component of an orthopedic implant or as an orthopedic implant.

401. An orthopedic implant comprising the osteoconductive polymer article according to embodiment 201 or 202.

402. An orthopedic implant comprising the osteoconductive polymer article according to embodiment 401 for use in partial or total joint arthroplasty, knee and hip prostheses, osteochondral implants, bone anchors, plugs, screws, meniscus or labrum replacement devices, or cartilage replacement devices.

The experiments and samples below further elucidate aspects and embodiments of the invention, but of course, should not be construed as in any way limiting the scope of the claims.

Experiments
Forming of Articles

Sample plates of 65*50*2 mm having a smooth surface were injection molded from Bionate® PCU 75D, an aliphatic polycarbonate polyurethane having Shore D hardness of about 73 and flexural modulus of about 1800 MPa (DSM Biomedical BV), applying a standard procedure and conditions for said polymer, and a mold with polished internal surfaces. Part of the polyurethane plates (IM1) were subsequently provided with a roughened or textured surface, by sandwiching plates between textured metal plates having a surface finish according to industry standard VDI 3400 (see www.vdi.eu) and PTFE foils, and compressing at 160° C. for 2.5 min at 50 kN using a Fontijne press (MP2-4).

Surface Roughness Measurement

The surface roughness of resulting molded plates was analyzed by white light interferometry using a Wyko NT100 profilometer (average of 5 measurements on an area of 1.8*2.4 mm with 2.5 magnification). In Table 1 surface roughness data for the molded plate samples are collected. Measured surface roughness of molded samples was found to be somewhat higher than nominal values of the textured molding plates.

TABLE 1

| sample | Surface roughness of textured molding plate used | Ra (µm) | Surface roughness of molded polyurethane plates Ra (µm) |
|---|---|---|---|
| IM1 | not | — | 0.10 |
| MP2 | VDI 3400 10 | 0.32 | 0.71 |
| MP3 | VDI 3400 36 | 6.30 | 8.40 |
| MP4 | VDI 3400 45 | 18.00 | 22.72 |

3D-printed porous sample plates were made from Bionate® 75D, the samples having porosity of about 40% and pore size of about 300 µm (designated PP5). The PP5 samples were found to have a compression modulus of about 57 MPA at 37° C. in water, suitably matching properties of subchondral bone.

Surface Modification of Articles

Samples were treated with simulated body fluids (SBF) for surface mineralization with calcium phosphate (CaP) in a series of experiments. Some initial testing with regular SBF showed only very slow mineralization, also for samples that had first been surface modified with oxygen plasma during 10 and 60 s. After observing that an untreated porous sample PP5 was not fully wetted with aqueous solutions, a 10 s oxygen plasma treatment using a March Plasma Systems PX500 apparatus was applied; such plasma-treated PP5 sample will be used hereafter. Further mineralization experiments were performed with SBF10, a solution having 10 times higher concentration than standard SBF; which resulted in fast and significant mineralization in periods of from 0.5 to 2.5 hrs. SEM images showed time-dependent mineralization, resulting in CaP crystals of about 10-100 µm on the surface. An initial adhesion assessment using a tape-test, however, showed easy removal of most of the crystals. As this would not be acceptable in a clinical setting, further tests were only performed on mineralized porous PP5 samples, as crystals within pores would not be easily eroded.

In another set of experiments samples were surface treated by dipcoating with suspensions of biphasic calcium phosphate particles (BCP, CamBioCeramics). This BCP contains about 81 mass % of hydroxyapatite (HA) and 19 mass % of β-tricalcium phosphate (bTCP). The material has a particle size distribution characterized by d50 of 5.9 µm and volume mean diameter of 6.8 µm. A suspension of 5 mass % BCP particles in tetrahydrofuran (THF) without further additives was made by vigorously stirring with a magnetic stirring bar, until shortly before use to prevent settling of particles. Dip-coating was performed with a PL3201 CooksonElectronics apparatus at room temperature within 45 s after stopping of stirring, using a draw speed of 10 mm/s. In case of multiple dipping steps, a drying time of 5 min between cycles was applied. After last dipping the sample was rinsed with ethanol and dried overnight at 40-60° C. under vacuum.

SEM images showed an increasing surface coverage of samples with the number of dipping steps. As an example, FIG. 1 shows 2, 4, 6 and 8 times dipped MP4 samples, revealing nearly full surface coverage after 8 dipping cycles.

A tape-test revealed strong adherence of BCP particles to the surface of the samples. This was also observed in tests wherein SBF-mineralized and BCP-coated molded samples were made into cylindrical rods of 1 cm length and 5.3 mm diameter. These rods were partially inserted with 5-10 beats into a 5.2 mm hole drilled in cadaveric bone. The bone was then sawed open to remove the rods, which were gently rinsed with ethanol to remove tissue debris and dried overnight at 60° C. under vacuum. SEM micrographs showed that SBF-coated rods had lost virtually all particles after insertion in the bone hole. On the BCP coated samples, however, particles were still present, much resembling the part that was not inserted into the bone; be it that a few craters were seen that likely resulting from removed particles. This confirms much better adhesion of particles on the polymer surface for the BCP/THF coating method vs SBF-coating.

Figure 2:
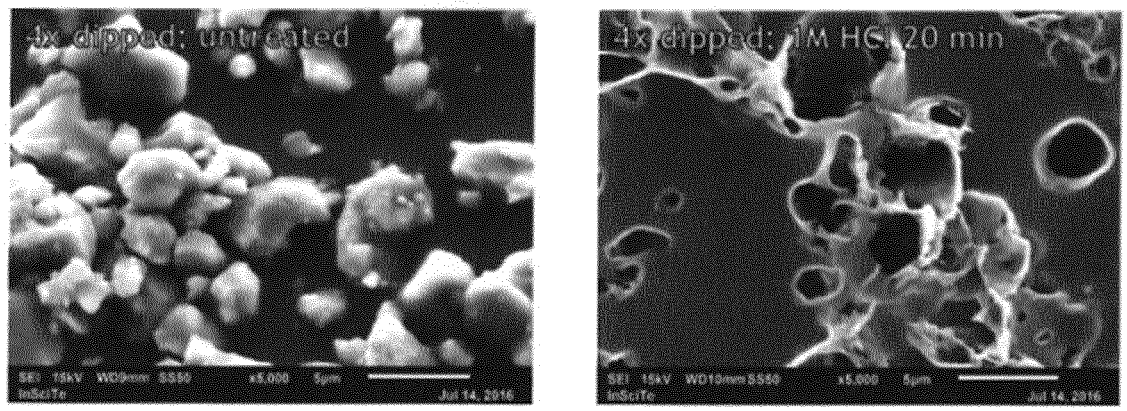
FIG. 2 shows SEM micrographs of the surface of a BCP-coated MP4 sample before (left) and after treatment with HCl solution.

In another test, the surface of dipped samples was treated with 1 M HCL solution to dissolve and/or remove BCP particles from the surface layer. In FIG. 2, SEM images of the surface of a 4-times dipped MP4 sample are shown before (left image) and after such treatment. BCP particles appear to be partly embedded in the polyurethane article, and still to be exposed on the surface. After treating with acid solution to dissolve the particles, the surface has crater-like structures with small protruding film-like edges. Apparently, the particles were effectively removed from the surface, whereas the observed thin edges suggest they were partly covered by polymer. A rationale given by the inventors is that THF, being a good solvent for the polyurethane material, swelled and/or partially dissolved polymer during the short dipping time only at a thin surface layer of the article, allowing particles to contact the swollen surface and to be partially covered by polymer during the dipping step and subsequent evaporation of at least part of the THF, thus 'freezing' the situation. By repeating such step, more particles are attached to the surface. This explains the observed good adhesion, and positive bioactivity results in the in vitro experiments discussed below.

During BCP/THF surface modification of the 3D-printed sample PP5 it was observed that the sample showed some shrinking. Such porous material has a larger surface area that is exposed to the THF solvent and observed dimensional change could be the result of THF more extensively swelling and softening the polymer throughout the porous article, enabling relaxation of stress built in during the printing process. Because such shrinkage was felt to be undesirably, but not observed for the molded samples MP2-4, a series experiments with different solvent compositions was performed on PP5 samples. The compositions used in the experiments are shown in Table 2, as well as shrinkage data (by measuring change in sample dimensions).

In experiments PP5-1.2-1.5 the samples were dip-coated in BCP suspensions as described above, using dispersions comprising THF and ethanol (EtOH). Such mixtures will be a less good or even a non-solvent for the polyurethane material. Addition of ethanol indeed reduces shrinkage and warpage, but the lower exposure to THF—which evaporates likely together with ethanol—also reduced embedding of particles in the surface. SEM evaluation showed presence of clusters of particles at the surface after dip-coating, but no craters in the surface after treating with 1M HCl.

In experiments PP5-1.6-1.9 the samples were dip-coated in BCP suspensions in ethanol, a non-solvent for polyurethane, followed by a post-dipping in pure THF with only drying in air (1.6) or with drying during a variable exposure time of up to 30 seconds followed by ethanol rinsing and drying steps (1.7-1.9). Exposing longer than 30 s after dipping to THF resulted in more shrinkage and warpage. This procedure would reduce exposure to good solvent, aiming to only swell a surface layer. Shrinkage and warpage indeed was reduced, but also embedding of particles in the surface was negatively affected, and clusters of particles were observed. Application of THF/EtOH as dispersion solvent in combination with a THF post-dipping step resulted in similar observations; see in Table 2 results for PP5-1.10-1.12. Further tests with methanol instead of ethanol had similar results.

Figure 3:
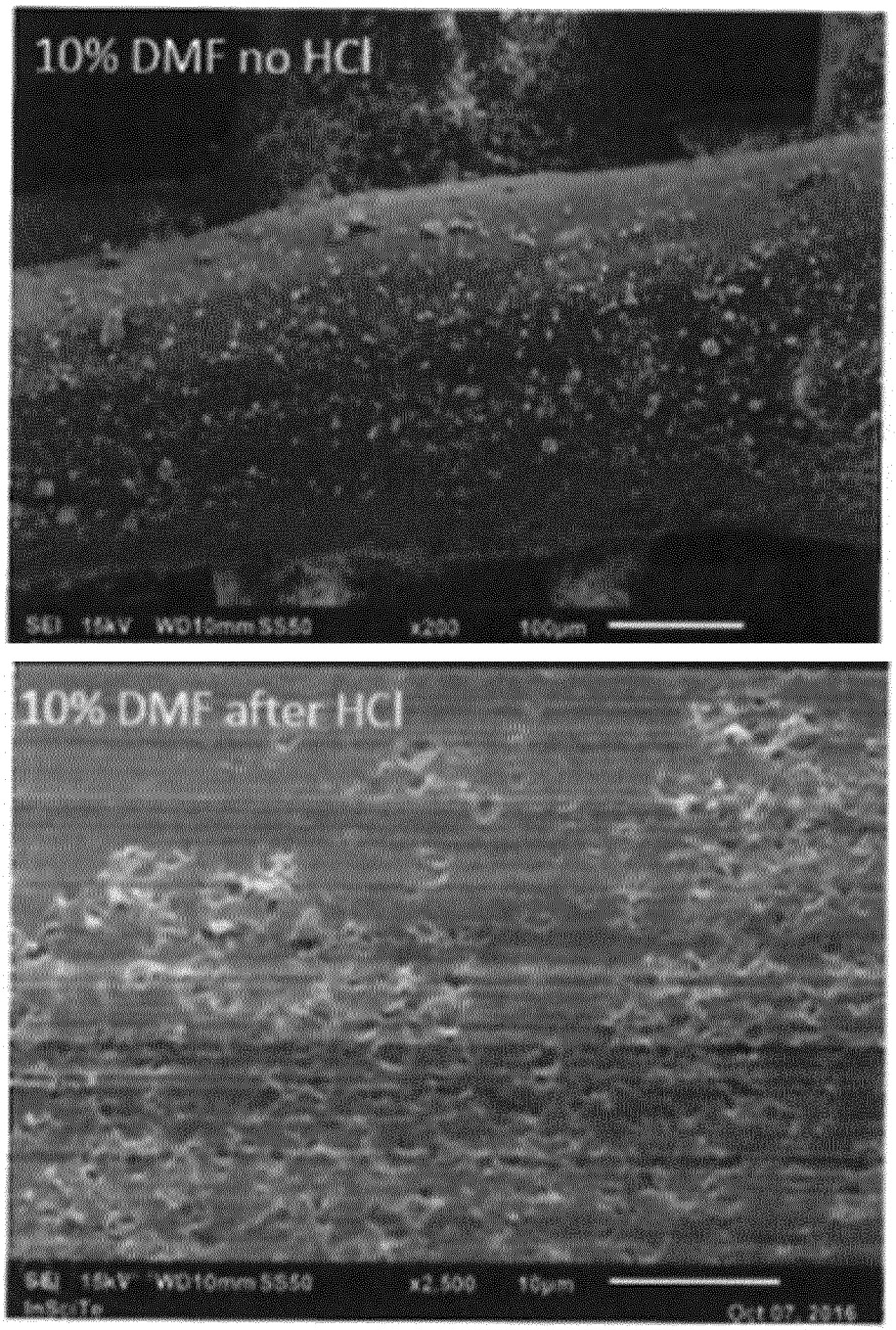
FIG. 3 shows SEM micrographs of PP5 samples that were surface treated with a BCP dispersion in DMF/EtOH 10/90, before (top figure) and after treatment with HCl solution.

In experiments PP5-2.1.-2.5 a dispersion of BCP in dimethylformamide (DMF) was applied. DMF is a good solvent for polyurethane with higher boiling point than THF. Using only DMF apparently resulted in such amounts of DMF on the porous article that the polymer structure started to dissolve within the time scale of the experiment. DMF/EtOH mixtures were tried with the idea that ethanol will evaporate from the mixtures, resulting in a relatively low amount of DMF with particles in contact with the polymer surface. Indeed, with mixtures comprising 2.5-10 vol % of DMF, shrinkage could be prevented or kept to a minimum, while the degree of particle adhesion also appears tunable; because more DMF in the mixture resulted in deeper pockets or craters being observed with SEM after treatment with HCl solution. FIG. 3 shows SEM micrographs on PP5 samples that were surface treated with BCP dispersions in 10/90 DMF/EtOH to illustrate such embedding of particles in the surface layer.

TABLE 2

Effect of solvent composition on shrinkage and surface modification of PP5

| Experiment | Solvent composition of BCP-dipping dispersion (volume/volume) | THF post-dip (s) | Shrinkage (%) | Remarks |
|---|---|---|---|---|
| PP5-1.1 | THF 100 | — | 15 | Warpage; surface embedded particles |
| PP5-1.2 | THF/EtOH 66/33 | — | 2 | Some warpage; no craters; clustered particles |
| PP5-1.3 | THF/EtOH 60/40 | — | 0 | No craters; clustered particles |
| PP5-1.4 | THF/EtOH 50/50 | — | 0 | No craters; clustered particles |
| PP5-1.5 | THF/EtOH 20/80 | — | 0 | No craters; clustered particles |
| PP5-1.6 | EtOH 100 | 5 + Air dried | 6 | Some warpage; no craters; clustered particles |
| PP5-1.7 | EtOH 100 | 5 + 0 | 0 | No craters; clustered particles |
| PP5-1.8 | EtOH 100 | 5 + 15 | 2 | No craters; clustered particles |
| PP5-1.9 | EtOH 100 | 5 + 30 | 6 | Some warpage; no craters; clustered particles |
| PP5-1.10 | THF/EtOH 50/50 | 5 + 0 | 2 | No craters; clustered particles |
| PP5-1.11 | THF/EtOH 50/50 | 5 + 15 | 3 | No craters; clustered particles |
| PP5-1.12 | THF/EtOH 50/50 | 5 + 30 | 4 | Some warpage; no craters; clustered particles |
| PP5-2.1 | DMF 100 | — | — | Polymer dissolves |
| PP5-2.2 | DMF/EtOH 50/50 | — | — | Polymer dissolves |
| PP5-2.3 | DMF/EtOH 10/90 | — | 1 | surface embedded particles |
| PP5-2.4 | DMF/EtOH 5/95 | — | 0 | surface embedded particles |
| PP5-2.5 | DMF/EtOH 2.5/97.5 | — | 0 | surface embedded particles |

In Vitro Testing of Bioactivity
Sample Preparation

For assessing of in vitro bioactivity of modified surfaces, samples were prepared by treating IM1, MP3, MP4 and PP5 samples with a BCP dispersion in THF following above described method, applying 2 and 8 dipping steps for the molded samples and 5 dipping steps for the printed sample. As references untreated IM1, MP2, MP3, and MP4 samples, oxygen-plasma treated PP5 with and without SBF10 treatment, as well as unmodified titanium (Ti) and a 12 wells plate (WP) were used. Test were performed at Maastricht University Medical Center.

Discs of diameter 20 mm and 2 mm thickness, fitting a well of well plates, were punched from the various samples and sequentially rinsed with demi-water, 96% ethanol, n-hexane, isopropanol and finally 96% ethanol. Each rinsing step was performed with 10 min ultrasonic treatment, followed by drying at 60° C. under vacuum after the final step. Coating was performed as described above, followed by drying at 60° C. under vacuum, and packaging in Wipak Medical Steriking SS1 pouches for 25 kGy gamma sterilization.

Cell Culture

Above-mentioned sample discs were placed in the wells of 12-well plates (Greiner Bio) under antiseptic conditions. Human bone marrow stem cells were cultured in T162 flasks prior to these experiments, and those reaching 70% confluency first were selected for use. Cells were seeded at a density of 5000 cells/cm$^2$ into the wells with 1000 µl proliferation medium per well. The proliferation medium consisted of alpha-MEM (Gibco), penicillin/streptomycine (Gibco) 1 vol % and embryotic serum (Millipore) 10 vol %. After 24 h of incubation on proliferation medium, all assays were done for baseline values. The proliferation medium was then replaced by osteogenic medium consisting of $10^{-8}$ M dexamethasone (Sigma), 0.01 M b-glycerol phosphate (Sigma), and 0.2 mM ascorbic acid (Sigma); and refreshed every 2-3 days.

Prestoblue Assay

PrestoBlue is a resazurin-based, membrane permeable solution that upon reduction forms resorufin, which is a red fluorescent compound that is quantitatively measured to determine cell viability. Such reduction process takes place in the mytochondria of healthy cells. Measured is the relative absorbance at 570 nm after 0, 7, 14 and 21 days.

AR-S Assay

Alizarine red-S (AR-S) staining is a common histochemical technique to detect calcium deposits in mineralized tissue and cultures, and positive AR-S staining for calcium has been shown to represent calcium phosphate and osteoblast culture mineralization. AR-S binds to deposited calcium. Mineralization is assessed by extraction of calcified mineral with a 10 vol % acetic acid solution, neutralization with ammonium hydroxide, and colorimetric detection at 4-5 nm in a 96-well format; after 0, 7, 14 and 21 days. Reported results are absolute values, corrected for cell free conditions.

Results

Experimental results after 21 days for the different assays are summarized in Table 3 (values between brackets represent standard deviation).

The BCP-coated samples showed positive activity in the AR-S tests, but at a similar level as non-coated samples and less than SBF-mineralized PP5 samples. This is likely related to the relatively large surface area of the mineralized porous material.

In the cell viability Prestoblue assay the BCP coated samples showed higher activity than non-coated references, and similar to the mineralized 3D-printed material.

Although there may be some limitations to this study, for example samples having rather different surface texture or porosity that may affect results, it can be concluded that the solvent-based surface modification method as presented herein can result in articles with bioactive inorganic particles well-adhered at the surface, and showing bioactivity enabling osseointegration as an orthopedic implant.

TABLE 3

Data of in vitro testing of samples

| sample | Prestoblue assay (relative value and (std)) | AR-S assay (relative value and (std)) |
| --- | --- | --- |
| MP2 | 0.080 (0.035) | 0.123 (0.029) |
| MP3 | 0.066 (0.082) | 0.317 (0.038) |
| MP4 | nd | 0.154 (0.093) |
| PP5-plasma | nd | 0.638 (0.020) |
| PP5-plasma-SBF | 0.259 (0.110) | 1.088 (0.126) |
| Ti | 0.216 (0.042) | 0.012 (0.004) |
| WP | 0.158 (0.031) | 0.081 (0.091) |
| MP2-BCP2 | 0.075 (0.031) | 0.160 (0.106) |
| MP2-BCP8 | 0.138 (0.095) | 0.049 (0.155) |
| MP3-BCP2 | 0.200 (0.055) | 0.147 (0.074) |
| MP3-BCP8 | 0.054 (0.060) | 0.342 (0.202) |
| MP4-BCP2 | 0.142 (0.033) | 0.258 (0.158) |
| MP4-BCP8 | 0.178 (0.091) | nd |
| PP5-BCP5 | 0.245 (0.061) | 0.169 (0.239) |

In Vivo Experiments

Implant Manufacturing

Sample implants were prepared in a two-step injection molding process, followed by applying a BCP coating and sterilizing. In the first step a substantially cylindrical implant stem of 6 mm diameter and length of 7 mm was prepared from Bionate® PCU 75D (DSM Biomedical BV), applying a standard procedure and conditions for said polymer, applying a mold with surface finish according to industry standard VDI 3400 36. In a second step the cylindrical implant stem was over-molded at one end with Bionate® PCU 80A (DSM Biomedical BV), applying a standard procedure and conditions for said polymer, using a mold having a double curved (R11, R18) smooth surface, resulting in a curved top layer with a thickness at the top of 2.5 mm and a diameter similar to that of the stem.

After injection molding, the implant articles were consecutively washed with water, ethanol, heptane, isopropanol, and again ethanol under ultrasonic conditions for 10 minutes. Then the articles were dried overnight at 80° C. and reduced pressure (<200 mbar) while maintaining a small $N_2$ flow (samples referred to as TPU).

Next the surface of the stem of a number of articles was treated by dipcoating with suspensions of biphasic calcium phosphate particles (BCP, CamBioCeramics). This BCP contains about 81 mass % of hydroxyapatite and 19 mass % of β-tricalcium phosphate, and has a particle size distribution characterized by d50 of 5.9 µm and volume mean diameter of 6.8 µm. A suspension of 5 mass % BCP particles in THF without further additives was made by vigorously stirring with a magnetic stirring bar, until shortly before use to prevent settling of particles. Dipcoating was performed by dipping the article in the BCP/THF suspension within 45 s after stirring was stopped, without covering the top surface made from lower hardness polyurethane. 6 subsequent dipping steps with a drying time of 5 min between cycles were applied. After last dipping the articles were rinsed with ethanol and dried overnight at 40-60° C. under vacuum (designated as BCP-TPU).

All coated implant articles were packed individually, directly after final overnight drying, in sterilization pouches and subsequently packed again in larger sterilization pouches. The double packaged articles were then sterilized using ethylene oxide gas (one ampule) on an Anprolene AN74i sterilizer during a standard 24 hours sterilization cycle, followed by a 2 hours aeration cycle. Sterilization was monitored by using an Anprolene AN87 dosimeter to ensure a minimal of 2000 mg/liter-hours exposure to the gas.

Surgical Procedure and Histological Processing

Twelve female Dutch milk goats were subject to this study; the average age of the goats at the time of surgery was 3.2±0.5 years) and the weight was on average 82.6±9.4 kg. This study was approved by the local and national Animal Ethical Committee under project license PV 2015-018. A medial parapatellar skin incision was made above the knee joint. The joint capsule was then opened exposing the medial femoral condyle. The center of the weight bearing part of the medial femoral condyle was located, and a bilateral osteochondral defect of 6.0 mm was created under K-wire guidance using a cannulated drill and custom-made surgical tools. The implant articles describe above were press-fit pushed into the defect (0.1 mm interference fit), with the curved softer top layer at the surface. Two polyurethane implant groups (solid injection molded implants with and without BCP-coating) and one metal implant group (positive control, referred to as metal) were included in this animal study (n=8 per group). Metal (titanium/cobalt/chromium) implants are known for their excellent osteointegrative properties and serve as a positive control for osseointegration.

Twelve weeks after surgery, the animals were euthanized by an intravenous overdose of 200 mg pentobarbital per kg bodyweight. The medial and lateral femoral condyle were consecutively cut out, placed in containers with neutral buffered formalin (NBF; 3.7 vol % formaldehyde in phosphate buffered saline) and stored at a rocking platform at 4° C. for at least 2 weeks. After fixation in NBF, medial femoral condyles were dehydrated by grading steps of ethanol using 50, 70, 96 and 100 vol % ethanol, each for 4 days. After dehydration, the medial femoral condyles were embedded in an epoxy resin (EpoThin 2, Buehler, Bluff, Ill., USA). The blocks were mounted in a diamond saw microtome (Leica SP1600), stained with Masson Goldner Trichrome stain (Carl Roth, Karsruhe, Germany), and sections of 50-70 μm were cut. The sections were visualised using bright light microscopy at 200-fold magnification. A custom written MATLAB script was used to determine the Bone Implant Contact (BIC), the percentage of the implant surface that is in direct contact with bone. Thresholding was applied to the red and green channels of the RGB-image to segment bone. The contours of the implant were drawn manually to determine the BIC, expressed as a percentage.

Results

Figure 4:
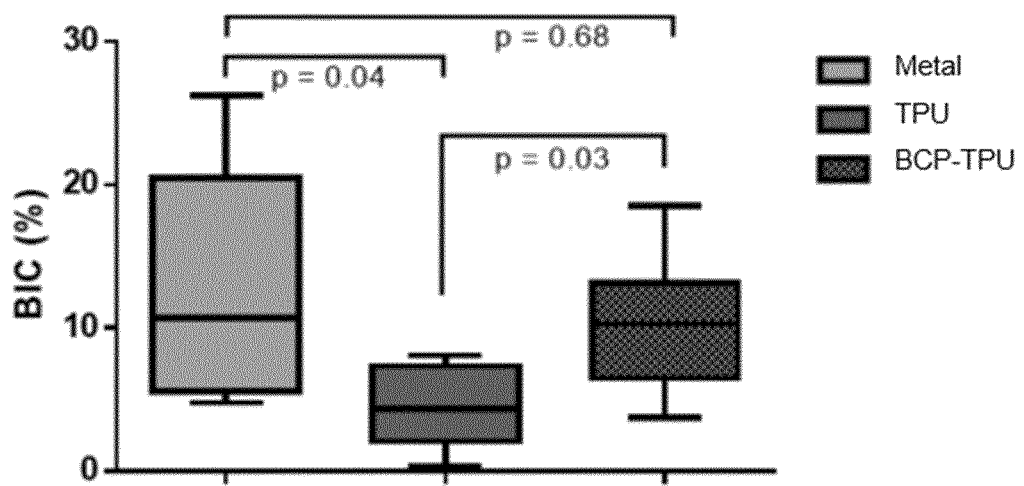
FIG. 4 represents histomorphometric analyses of osseointegration of 3 different implants using bone-implant contact (BIC) percentage.

The BIC percentage for BCP-coated polyurethane implants (BCP-TPU) did not significantly differ from metal implants (p=0.68). The difference between the uncoated implant group and both the metal implant and BCP-coated implant group was statistically significant (p=0.04, p=0.03 respectively), clearly illustrating the beneficial effect of the bioceramic particle coating in combination with polyurethane surface of certain roughness on osseointegration (see FIG. 4).

Figure 5:
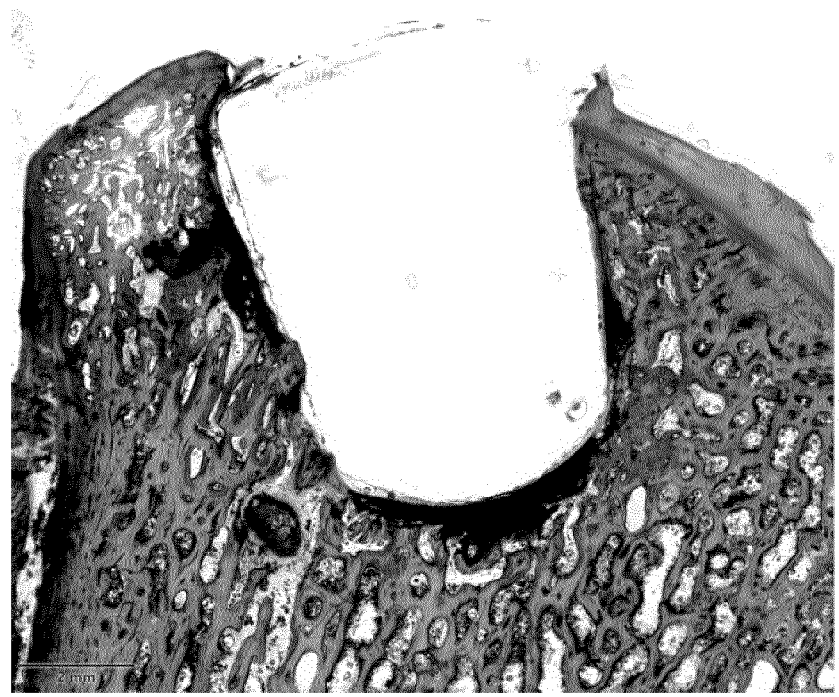
FIGS. 5A and 5B show optical micrographs of histological slices for uncoated (A) and BCP-coated (B) polyurethane implants.
Figure 5:
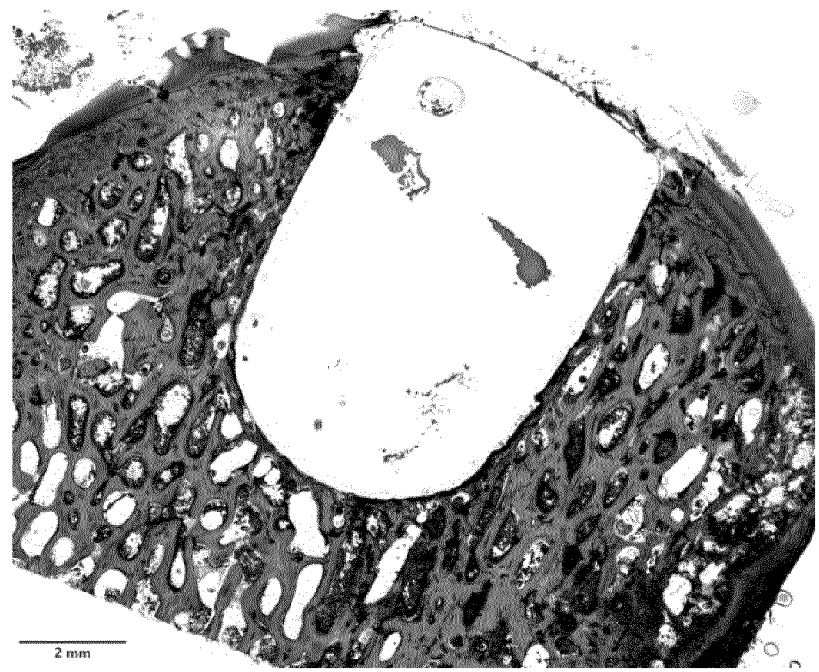

In histological slices, a fibrous tissue layer can be typically observed between the uncoated implant TPU and bone, and a blurred, indistinct transition between bone and implant (see FIG. 5A). In contrast, no such layer and a clearly delineated and well-defined implant-bone transition can be observed for the coated implants BCP-TPU (see FIG. 5B).

Unless stated otherwise, any expression of mass % is based on the mass of the entire composition. It is noted that weight is still frequently used in the art instead of mass; mass and weight may herein be used interchangeably unless clearly contradicted by context.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as" or "like") provided herein, is intended merely to better illustrate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. While certain optional features are described as embodiments of the invention, the description is meant to encompass and specifically disclose all combinations of these embodiments unless specifically indicated otherwise or physically impossible.

The invention claimed is:

1. A method of making an osteoconductive polymer article for use as an orthopedic implant comprising the steps of:
   a. providing an article comprising a biocompatible, non-biodegradable polymer, the article comprising a non-flat surface with roughness Ra of at least 5 μm;
   b. providing a dispersion of bioactive ceramic particles of particle size of at most 10 μm in a first solvent comprising a solvent for the polymer;
   c. coating at least the non-flat surface with the dispersion in at least one step, thereby forming a coated article; and
   d. rinsing the coated article with a second solvent being a non-solvent for the polymer to substantially remove the first solvent, thereby obtaining an article comprising bioactive ceramic particles partly embedded in the polymer at the surface of the article.

2. The method according to claim 1, wherein the article is non-porous and the non-flat surface is a textured surface having a roughness Ra of at least 10 μm.

3. The method according to claim 1, wherein the article is porous and comprises pores having an average pore size of 50-500 μm.

4. The method according to claim 1, wherein the polymer is a thermoplastic elastomer.

5. The method according to claim 1, wherein the polymer is a polyurethane block copolymer.

6. The method according to claim 5, wherein the polyurethane block copolymer comprises an aliphatic polycarbonate as soft block.

7. The method according to claim 5, wherein the polyurethane block copolymer has a durometer hardness as measured with the Shore test of from 40 ShA to 80 Shd.

8. The method according to claim 1, wherein the polymer is block copolymer comprising a soft block with a Tg of lower than 0° C.

9. The method according to claim 1, wherein the ceramic particles comprise calcium phosphate or a bioactive glass.

10. The method according to claim 1, wherein the dispersion comprises 1-15 mass % of ceramic particles.

11. The method according to claim 1, wherein the first solvent comprises a solvent for the polymer and a non-solvent for the polymer.

12. The method according to claim 11, wherein the non-solvent for the polymer has a lower boiling point than the solvent for the polymer.

13. The method according to claim 1, wherein the dispersion does not contain dispersion aids or surfactants.

14. The method according to claim 1, wherein the coating is done by dip coating or spray coating.

15. The method according to claim 14, further comprising the step of drying the coating after coating at least the non-flat surface with the dispersion.

16. The method according to claim 15, further comprising the step of again coating at least the non-flat surface with the dispersion and drying the coating prior to rinsing the coated article.

17. The method according to claim 16, wherein the first coating is done by applying a dispersion comprising bioceramic particles having a first particle size and the second coating is done by applying a dispersion comprising bioceramic particles having a second particle size, wherein the first particle size is greater than the second particle size.

18. The method according to claim 1, wherein the article provided in step a. a consists of a biocompatible, non-biodegradable polymer.

19. The method according to claim 1, wherein the bioactive ceramic particles have a size of from 200 nm to 5 µm.

\* \* \* \* \*